(12) United States Patent
Barbul et al.

(10) Patent No.: US 11,543,381 B2
(45) Date of Patent: Jan. 3, 2023

(54) METHOD AND APPARATUS FOR OPERATING A GAS SENSOR

(71) Applicant: TDK Corporation, Tokyo (JP)

(72) Inventors: Andreas Barbul, Munich (DE); Matthias König, Munich (DE)

(73) Assignee: TDK Corporation, Tokyo (JP)

( * ) Notice: Subject to any disclaimer, the term of this patent is extended or adjusted under 35 U.S.C. 154(b) by 200 days.

(21) Appl. No.: 16/913,793

(22) Filed: Jun. 26, 2020

(65) Prior Publication Data

US 2020/0408713 A1 Dec. 31, 2020

(30) Foreign Application Priority Data

Jun. 27, 2019 (DE) .......................... 102019117405.8

(51) Int. Cl.
| | | |
|---|---|---|
| *G01N 27/414* | (2006.01) | |
| *G01N 33/00* | (2006.01) | |
| *G06N 3/04* | (2006.01) | |
| *G06N 3/08* | (2006.01) | |
| *G06N 3/063* | (2006.01) | |

(52) U.S. Cl.
CPC ..... *G01N 27/4148* (2013.01); *G01N 33/0062* (2013.01); *G06N 3/04* (2013.01); *G06N 3/0635* (2013.01); *G06N 3/08* (2013.01)

(58) Field of Classification Search
CPC .......... G01N 27/4148; G01N 33/0062; G01N 33/0031; G01N 21/3504; G01N 27/4175; G01N 30/30; G01N 2291/02881; G06N 3/04; G06N 3/08; G06N 3/02; H04L 27/08; H04L 27/366; H02H 1/0092; F01D 21/003; F01D 17/02; G01D 3/022; G01D 18/00

USPC .......... 73/1.06, 23.2, 31.05; 340/632; 702/1, 702/22–24, 33, 47, 85, 104, 130, 702/182–183, 189; 706/15, 20, 25, 31
See application file for complete search history.

(56) References Cited

U.S. PATENT DOCUMENTS

| | | | | |
|---|---|---|---|---|
| 6,366,896 | B1 * | 4/2002 | Hutchison | ............... G06N 3/02 706/14 |
| 6,754,644 | B1 * | 6/2004 | Hutchison | ............... G06N 3/08 706/14 |
| 2005/0063873 | A1 * | 3/2005 | Morris | ............... G01N 33/0031 422/98 |
| 2005/0171702 | A1 * | 8/2005 | Calabrese | ......... H01L 21/67253 702/24 |
| 2006/0059924 | A1 * | 3/2006 | Horan | ..................... F25B 45/00 374/E7.042 |

(Continued)

FOREIGN PATENT DOCUMENTS

CN 204666549 U * 9/2015

*Primary Examiner* — Jeffrey P Aiello
(74) *Attorney, Agent, or Firm* — Slater Matsil, LLP

(57) ABSTRACT

A method and apparatus for operating a gas sensor are disclosed. In an embodiment a method for operating a gas sensor includes providing, by at least one gas sensor element, a sensing signal and correcting, by a neural network, the sensing signal, wherein the neural network comprises an input layer, an output layer and at least one hidden layer, wherein the input layer comprises a given number k>1 of input neurons for each gas sensor element, and wherein a respective gas sensor element provides its sensing signal to one of the corresponding input neurons dependent on a measurement parameter applied to the at least one gas sensor element.

13 Claims, 4 Drawing Sheets

(56) References Cited

U.S. PATENT DOCUMENTS

| | | | |
|---|---|---|---|
| 2006/0059925 A1* | 3/2006 | Horan | B60H 1/00585 |
| | | | 62/208 |
| 2011/0191058 A1* | 8/2011 | Nielsen | G01C 15/02 |
| | | | 702/141 |
| 2018/0036559 A1 | 2/2018 | Ishiji et al. | |
| 2019/0048810 A1* | 2/2019 | Taglialatela Scafati | |
| | | | F02D 41/1467 |
| 2019/0121338 A1* | 4/2019 | Celia | G05B 23/0294 |

* cited by examiner

METHOD AND APPARATUS FOR OPERATING A GAS SENSOR

CROSS-REFERENCE TO RELATED APPLICATIONS

This application claims priority to German Application No. 102019117405.8, filed on Jun. 27, 2019, which application is hereby incorporated herein by reference.

TECHNICAL FIELD

The present invention relates to a method and an apparatus for operating a gas sensor. Additionally the present invention relates to a gas sensor.

BACKGROUND

More and more sensors are being used in smartphones. Most of them have a human counterpart:

Eyes↔camera, ears↔microphone, sense of touch↔touchscreen, sense of balance↔gyroscope etc.

What is still missing is the sense of smell. Recently new miniaturized gas sensors capable of detecting different gases have been introduced, which are cheap and small. In many applications it is sufficient to just measure one gas. But from an application perspective it is much more interesting to detect more than one gas. There are many different ways of building such a multi-gas sensor. However, today's gas sensors are either very complex or not very reliable.

SUMMARY

Embodiments provide a method and an apparatus for operating a gas sensor allowing for a reliable detection of one or more gases while at the same time allowing a compact chip and/or package size.

According to a first and second aspect, embodiments provide a method and a corresponding apparatus for operating a gas sensor comprising at least one gas sensor element, which is configured to provide a sensing signal. The gas sensor is operated by using a neural network for correcting the sensing signal of the at least one gas sensor element. The neural network comprises an input layer, an output layer and at least one hidden layer, wherein the input layer comprises for the at least one gas sensor element, preferable for each gas sensor element, a given number k>1 of input neurons and the respective gas sensor element is configured to provide its sensing signal to one of these corresponding input neurons dependent on a measurement parameter applied to the gas sensor element. Thus, different neurons are used for different sensing signals of one gas sensor element, wherein the difference of the sensing signals relates the measurement parameter.

The gas sensor elements are configured to provide a sensing signal. In the case where the gas sensor element is configured to detect a specific gas, the sensor signal of the gas sensor element is dependent on a kind of gas the senor element is exposed to. In the case where the gas sensor element is configured to sense a specific gas, the sensor signal of the gas sensor element is dependent on a concentration of the specific gas the gas sensor element is exposed to. In particular, the sensor signals comprise current values or voltage values. The sensor values of the gas sensor elements are representative of the provided sensor signals output by the gas sensor elements.

By extending the neural network by using the respective gas sensor elements as multiple neurons, a faster detection rate can be achieved and an "on-the-fly" gas detection rate can be improved. Furthermore cost savings can be achieved as fewer gas sensor elements can be used for a similar detection rate. Each sensor can be assigned to a new measurement parameter value, for example to a new temperature, to improve the detection rate of desired gases or scents.

In an embodiment according to the first and second aspect, the gas sensor is operable in a learning mode, in which the neural network adjusted with random feedback loops between directly adjacent layers is used.

This algorithm is used with a random change of the weighting of one or more neurons. The random change of the weighting may concern the change of the temperature and thus the weighting which is calculated, for example by an ASIC, from it. Random temperature values are generated, for example by the ASIC, which are stored in a temperature tensor. The heating voltage of gas sensor heaters are controlled, for example by the ASIC. For instance the ASIC or another control unit sets the voltage which sets the temperature required. From this, further weightings are calculated, which then achieve a result in the neuronal network, i. e., a certain output is provided by the neuronal network. This result can then be compared with reference values and the detected gas mixture can be identified. The reference values can be obtained from a calibration or from a cloud computing infrastructure.

In a further embodiment according to the first and second aspect, the random feedback loops comprise different temperature values or are relate to different temperature values. This allows for improving the gas detection rate as temperature variations and fluctuations mainly influence the measurement results of the gas sensor elements, in particular with regard to semiconductor metal oxide layer gas sensor elements. Thus, the gas sensor elements can be operated without monitoring the temperature of the gas sensor element by means of a temperature sensor.

In a further embodiment according to the first and second aspect, the random feedback loops comprise different electrical field strength values or relate to different electrical field strength values. This allows for improving the gas detection rate as electrical field strength variations and fluctuations mainly influence the measurement results of the gas sensor elements, in particular with regard to gas sensor elements comprising electrically conductive polymers. Thus, the gas sensor elements can be operated without monitoring the electrical field strength applied to the gas sensor element with an additional sensor.

In a further embodiment according to the first and second aspect, the gas sensor is operable in a normal operation mode, in which the neural network with a feedforward structure is used.

In a further embodiment according to the first and second aspect, the at least one gas sensor element comprises a semiconductor substrate with a metal oxide sensing layer.

In a further embodiment according to the first and second aspect, the at least one gas sensor element comprises electrically conductive polymers.

In a further embodiment according to the first and second aspect, the measurement parameter applied to the at least one gas sensor element is representative of a temperature of the sensing layer of the sensing element.

In a further embodiment according to the first and second aspect, the measurement parameter applied to the at least one gas sensor element is representative of an electrical field strength.

In a further embodiment according to the second aspect, the apparatus comprises an application-specific integrated circuit (ASIC) which is configured to provide the random feedback weights to the neural network. A logic of the neuron matrix calculations is normally implanted on a device which operates a CPU to calculate the weights of the neurons and train the neural network. By using such an ASIC, which preferably also powers the gas sensor and measures and/or captures the sensing signals of the at least one gas sensor element, a faster detection rate can be achieved.

In a further embodiment according to the second aspect, the application-specific integrated circuit is configured to execute the processing of the trained neural network in the normal operation mode of the gas sensor.

In a further embodiment according to the second aspect, the application-specific integrated circuit is configured to provide learning data and to provide the random feedback weights for the random feedback loops to the neural network for executing the processing of the neural network in the learning mode. The learning data, in particular comparative values, can be obtained from reference values of a calibration or from a cloud computing infrastructure.

Advantageously, such an ASIC can operate on its own without requiring a second device to decide how to detect possible new concentrations of gases. Thus, a second device is not needed or power consumption of the second device can be reduced.

According to a third aspect, embodiments provide a gas sensor system comprising at least one gas sensor element which is configured to provide a sensing signal and an apparatus according to the second aspect.

Optional embodiments of the first and second aspect shall apply here also to the further aspects.

In an embodiment according to the third aspect, the gas sensor system comprises a processing unit configured to operate the gas sensor in the normal operation mode and/or in the learning mode and/or in a basic training mode, wherein in the basic training mode an error backpropagation algorithm is used for the neural network to determine the weights of the neural network.

It is possible that the temperatures of all sensor elements are varied. Alternatively, it is also possible that only individual sensor elements can be affected. In other words, 10 gas sensor elements that form 10 neurons, the temperatures can also only be varied at one or x temperatures. Preferably 10×10 possibilities at neurons are used.

Optional embodiments of the first and second aspect shall apply here also to the further aspects.

BRIEF DESCRIPTION OF THE DRAWINGS

In the following, the present invention is described in detail with reference to the figures. These are as follows.

DETAILED DESCRIPTION OF ILLUSTRATIVE EMBODIMENTS

Figure 1:
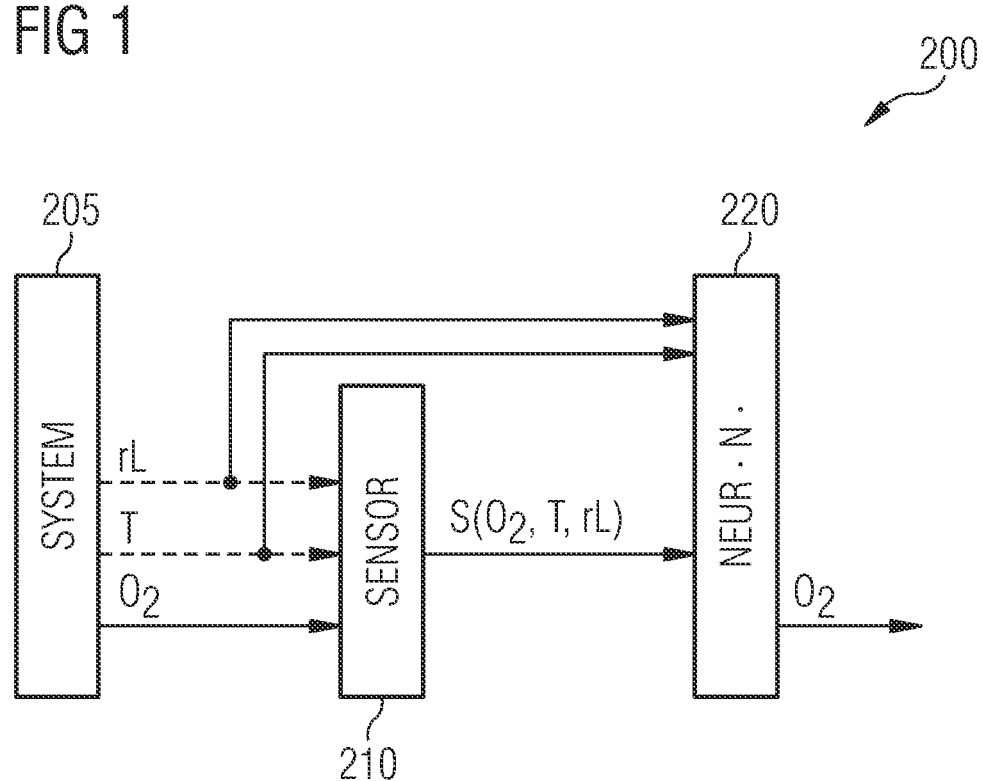
FIG. 1 a schematic block diagram of a gas sensor according to the prior art.

Elements of the same design and function that appear in different figures are identified by the same reference numerals.

FIG. 1 shows a schematic block diagram of an oxygen sensor system 200 according to the prior art. The oxygen sensor 210 provides a sensing signal which depends on a concentration of oxygen, a temperature and a relative air humidity.

A neural network 220 is used for sensing signal correction. The neural network 220 comprises an input neuron for a gas sensing signal, and further input neurons for temperature and relative air humidity. However, such a system 205 requires additional sensors, in particular a temperature sensor and a relative air humidity sensor, which provide the respective sensor signals.

In order to be able to do without additional sensors, semiconductor metal oxide sensors with a heating element are introduced, so that the semiconductor gas sensor element GS1, GS2, GS3 can be heated to a certain temperature. The heating element is heated up in a controlled manner, i.e. a certain amount of energy is supplied to the heating element so that it normally heats up to a certain temperature. There is no monitoring of whether the heating element actually heats up the gas sensor element GS1, GS2, GS3 to the desired temperature. Thus, if such sensors are used at very different temperatures or boundary conditions, deviations in the temperature of the gas sensor element GS1, GS2, GS3 can occur, which can lead to errors in the measured gas concentration and/or gas detection.

Figure 2:
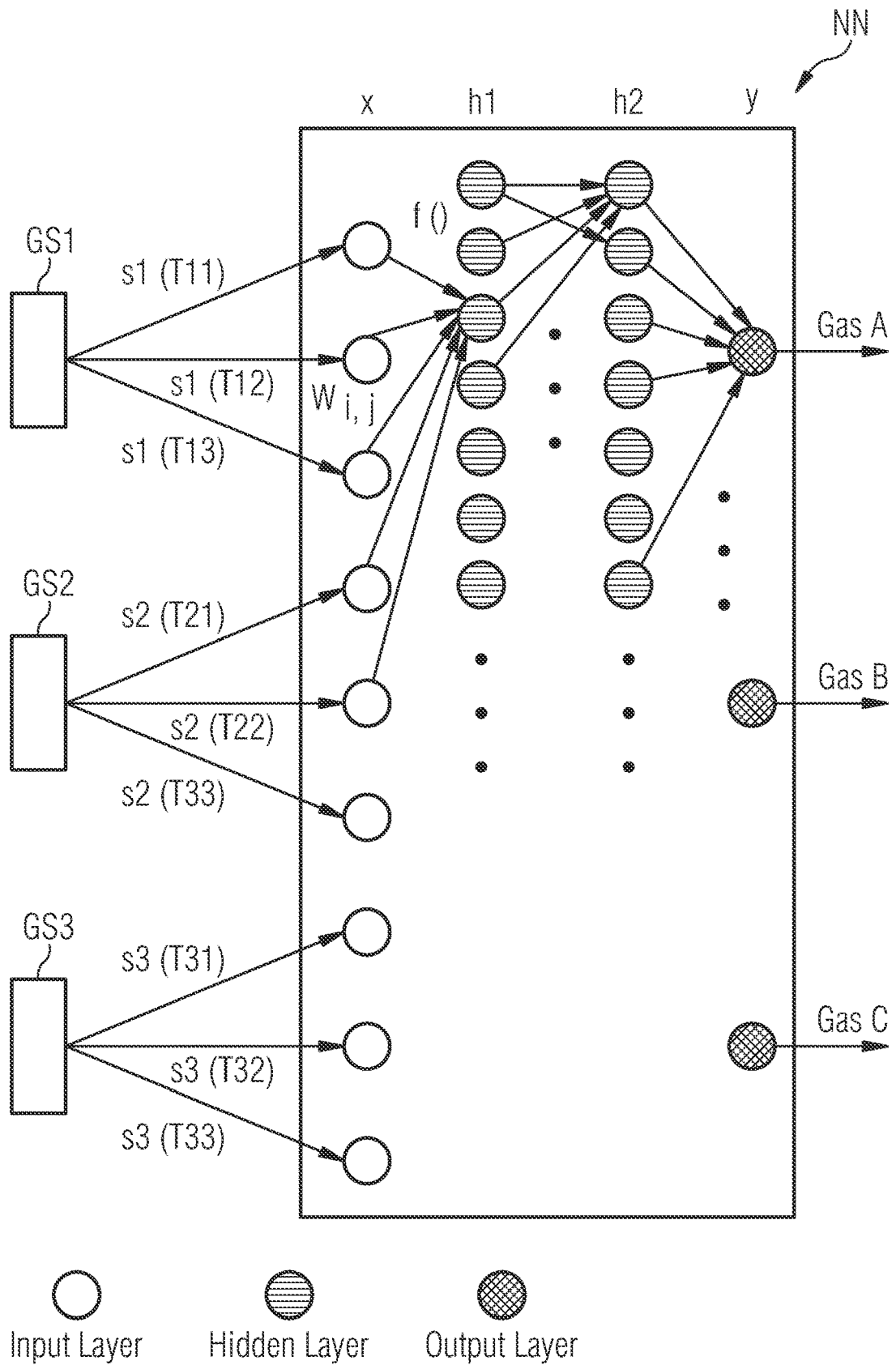
FIG. 2 an exemplary embodiment of a neural network.

FIG. 2 shows a gas sensor 2 and an exemplary embodiment of a neural network NN fed by an exemplary gas sensor 2.

The neural network NN comprises a large number of neurons. The neurons have one or more inputs. To calculate their output value, first a sum of all input values $x_i$ multiplied by the weighting factor $w_i$ is calculated. The output value is then calculated by applying an activation function f of the respective neuron to this sum. The activation function performs the important task of enabling nonlinear relationships between input values and output values. As the activation function f different functions can be used, e.g. a linear, Heaviside step function, logistic sigmoid function, fsigmoid, gauss or hyperbolic tangent function.

These artificial neurons are combined into networks consisting of several neurons arranged in layers.

The gas sensor 2 shown in FIG. 2 comprises at least one gas sensor element GS1, GS2, GS3 configured to provide a sensing signal s1, s2, s3. The gas sensor 2 is for example a semiconductor metal oxide gas sensor and the at least one gas sensor element GS1, GS2, GS3 of the gas sensor 2 comprises, for example, a semiconductor metal oxide sensing layer.

Alternatively the gas sensor 2 is for example an organic semiconductor gas sensor and the at least one gas sensor element GS1, GS2, GS3 comprises electrically conductive polymers.

In the example shown in FIG. 2, the gas sensor 2 comprises three gas sensor elements GS1, GS2, GS3. For correcting the sensing signal s1, s2, s3 of the at least one gas sensor element GS1, GS2, GS3, a neural network NN with an input layer, an output layer and at least one hidden layer is used. The neural network NN according to FIG. 2 comprises for example two hidden layers.

The input layer comprises for each gas sensor element GS1, GS2, GS3 a given number k>1 of input neurons, and the respective gas sensor element GS1, GS2, GS3 is configured to provide its sensing signal s1, s2, s3 to one of these corresponding input neurons dependent on a measurement parameter applied to the gas sensor element GS1, GS2, GS3.

For example, the input layer comprises for each gas sensor element GS1, GS2, GS3 a given number of input neurons, wherein each of these input neurons is provided with a sensing signal s1, s2, s3 of the corresponding gas sensor element GS1, GS2, GS3 captured or measured at different temperatures of the gas sensor element GS1, GS2, GS3.

This means that a first input neuron receives a sensing signal s1, s2, s3 provided by the gas sensor element GS1, GS2, GS3 when the provided heating energy corresponds to a first temperature of the gas sensor element GS1, GS2, GS3 or to a temperature of the gas sensor element GS1, GS2, GS3 within a first temperature range. A second input neuron receives a sensing signal s1, s2, s3 provided by the gas sensor element GS1, GS2, GS3 when the provided heating energy corresponds to a second temperature of the gas sensor element GS1, GS2, GS3 or to a temperature of the gas sensor element GS1, GS2, GS3 within a second temperature range.

Alternatively or optionally the measurement parameter is an electrical field strength.

Thus, each gas sensor element GS1, GS2, GS3 can be used as multiple neurons.

Stored temperature tensors generate the various neurons. Already learned temperature tensors and, depending on the result, random temperature tensors are used. Different temperatures are used in time intervals for example from 1 ms to 1 h. Each sensor element can be assigned a new temperature value during feedback or for a new gas.

In a preferred embodiment, the gas sensor 2 is configured to be operated in a basic training mode, a normal operation mode and in a learning mode.

For instance, in a normal operation mode, a trained neural network NN is used to correct the sensing signal s1, s2, s3 of the gas sensor 2. The trained neural network NN of the gas sensor 2 comprises for example a feedforward network structure.

FIGS. 3a to 3d show different neural network topologies. In FIGS. 3a to 3d, the dotted arrows describe the forward propagation, while the black arrows describe the backward propagation and the learning process, respectively. For normal operation only the forward path is used.

For the neural networks NN shown in FIGS. 3a to 3d, for the forward path the behaviour of such a network can be mathematically described by the following equations Eq. (1) to (3), wherein the weights are determined during a preceding training phase.

$$a_1 = W_1 x + b_1, h_1 = f(a_1) \quad \text{Eq. (1)}$$

$$a_2 = W_2 h_1 + b_2, h_2 = f(a_2) \quad \text{Eq. (2)}$$

$$a_y = W_y h_2 + b_2, \hat{y} = f_y(a_y) \quad \text{Eq. (3)}$$

wherein x is the input to the network, y is the output of the network, $h_1$, $h_2$ are hidden activity vectors, $W_1$ is the matrix of synaptic weights from x to $h_1$, $W_2$ is the matrix of synaptic weights from $h_1$ to $h_2$, and $W_3$ is the matrix of synaptic weights from $h_2$ to y, f( ) are activation functions.

Before such a network can be used for prediction or correction, it must be trained. This means that the weightings wij from neuron i to neuron j must be set on the basis of a reference data set, also named training data set, so that the desired results are obtained at the initial neurons of the neural network NN.

Different learning algorithms can be used to train the networks. FIG. 3a shows an error backpropagation algorithm.

With the error backpropagation algorithm, the weightings are initially set randomly. The input values of the training data are then presented to the network, the output values of the neural network NN are calculated and compared with the target output values of the training data. An error is then minimized backwards (from the output neurons to the input neurons) by adjusting the weightings. This process is repeated until, for example, a mean square error (MSE) on the entire training data set or an independent test data set is smaller, or a certain number of training data passes has been reached. The "knowledge" or the calibration information is thus given by the topology of the network and the weightings w.

FIG. 3a shows a neural network NN with backpropagation (black row).

If a logistic activation function in the output layer and a binary cross-entropy loss function is chosen, the loss for a mini-batch with size N and the gradient at the output layer e are calculated as $$J = -\frac{1}{N} \sum_{m,n} y_{mn} \log \hat{y}_{mn} + (1 - y_{mn}) \log(1 - \hat{y}_{mn}) \quad \text{Eq. (4)}$$

$$e = \delta a_y = \frac{\partial J}{\partial a_y} = \hat{y} - y \quad \text{Eq. (5)}$$

where m and n are output unit und mini-batch indexes. For the backpropagation (BP), the gradients for hidden layers are calculated as $$\delta a_2 = \frac{\partial J}{\delta a_2} = (W_3^T e) \odot f'(a_2), \quad \text{Eq. (6)}$$

$$\delta a_1 = \frac{\partial J}{\delta a_1} = (W_2^T \delta a_2) \odot f'(a_1)$$

Where $\odot$ is an element-wise multiplication operator and f'( ) is the derivative of the non-linearity f( ). This gradient is also called steepest descent, because it directly minimizes the loss function given the linearized version of the network.

It can be learned that backpropagation multiplies error signals by the transposed weighting matrix $W^T$. This implies that the feedback is computed using the knowledge of all the synaptic weights in the forward path. Thus the computational effort is very high.

Therefore, preferably the gas sensor 2 is configured to be operated in the basic training mode, a normal operation mode and in the learning mode.

During the basic training mode, in particular the error backpropagation algorithm is used.

For example, prior to shipment of the gas sensor 2 or after a basic reset of the gas sensor 2, the neural network NN of the gas sensor 2 is operated in the basic training mode, where it is operated with an error backpropagation algorithm.

Figure 4:
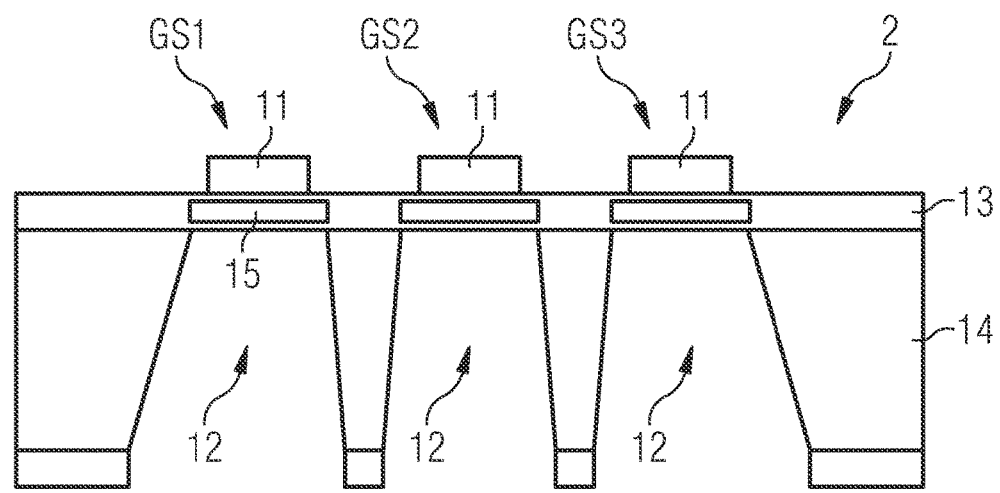
FIG. 4 a cross section of an exemplary gas sensor element.

FIG. 4 show a cross section of an exemplary multi-gas sensor 2. The multi-gas sensor 2 comprises multiple gas sensor elements GS1, GS2, GS3. The multi-gas sensor 2 shown in FIG. 4, for example, comprises three gas sensor elements GS1, GS2, GS3. The multi-gas sensor 2 is for example a semiconductor gas sensor.

Semiconductor gas sensors rely on a gas coming into contact with a metal oxide surface and then undergo either oxidation or reduction. Absorption or desorption of the gas on the metal oxide changes either the conductivity or resistivity from a known baseline value. This change in conductivity or resistivity can be measured with electronic circuitry.

The metal oxide surface is usually a thin film of a transition or heavy metal. The exact metal that is used will depend on the application; examples of metals include tin dioxide (SnO2) or tungsten oxide (WO3). The film overlies a layer of silicon and is heated to a temperature between 200 and 400° C., again depending on the application. In this way, the chemical process is accelerated and the effects of fluctuating external temperatures are minimised.

The respective gas sensor element GS1, GS2, GS3 shown in FIG. 4 comprises for example a sensing layer 11 of metal oxide. The gas sensor elements GS1, GS2, GS3 comprise a metal oxide layer or a metal oxide meander. The gas sensor elements GS1, GS2, GS3 are, for instance, integrated with a CMOS circuitry (not shown) on a single chip. A stack of layers 13 is arranged on a semiconductor substrate 14 required for the CMOS circuitry. The respective gas sensor element GS1, GS2, GS3 comprises a membrane. A portion of the semiconductor substrate 14 is, for instance, etched away to form a cavity 12 at the location of the sensing layer 11. Remaining layers 13 and possibly a remaining portion of the substrate 14 form a thin membrane to support the layer 11.

The respective gas sensor element GS1, GS2, GS3 comprises a heating element 15. The heating element 15 is embedded within the layer 13 and comprises conducting elements. The heating element 15 is configured to provide a local source of heat to heat the metal oxide layer 11 e.g. during operation of the gas sensor element GS1, GS2, GS3. The temperature can rise rapidly around the metal oxide layer 11 on the membrane, while a thicker part of the gas sensor chip, i.e. the portion where the substrate 14 is not removed, reacts with a slower temperature rise due to its thermal inertia. By controlling the heating element 15 accordingly, the metal oxide layer 11 can be activated for a measurement and be regenerated afterwards.

Each of the metal oxide layers 11 is contacted by two conductive electrodes and hence acts as a resistor. In the presence of a compound its resistance changes, thereby providing a measure of a concentration of the compound in the immediate vicinity of the metal oxide sensing layer 11.

Both the conductive electrodes and the heating element 15 are preferably connected to a control unit, which can be implemented as a part of the CMOS circuitry arranged on the same substrate 14.

Gas sensors have to be calibrated. The output signals of the gas sensor elements GS1, GS2, GS3 are generally in the form of a voltage value. Calibration is needed to implement a relation between the gas sensor element GS1, GS2, GS3 signal and the concentration level of the corresponding gas.

Because of manufacturing tolerances it is not possible to produce exact copies of a gas sensor 2 in a production process. There are always small fluctuations in the provided output signals. This is the reason why nearly all gas sensor products need to be calibrated after assembly. This means that calibration data is determined and used during operation of the gas sensor 2 to adjust the sensor signals of the gas sensor elements GS1, GS2, GS3 to provide accurate measurement output signals.

As the gas sensors 2 are used differently, in particular in different environments, in particular in different kind of smart phones or in kitchen or medicine equipment, the neural network NN has to be implemented and/or trained and/or further trained by the user of the gas sensor 2 himself. However, such training often relies on inexact temperature data and a full powered CPU is required.

Therefore, it is proposed to provide a gas sensor system 1 in which the gas sensor 2 is, besides the normal operation mode, operable in the learning mode. The learning mode can be used to basically train the neural network NN of the gas sensor 2 and/or the learning mode can be used to further train the already trained neural network NN of the gas sensor 2.

The trained neural network NN can be a basically trained neural network or a neural network NN which has been basically trained and further trained once or several times by applying the learning mode.

In the learning mode the neural network NN uses random feedback loops, wherein the neural network NN can be untrained or basically trained or further trained. In this way the neural network NN can learn to extract useful information from signals sent through these random feedback connections. In essence, the network learns to learn. Such a mechanism works as quickly and accurately as backpropagation.

In the learning mode each gas sensor element GS1, GS2, GS3 is used as multiple neurons. Each gas sensor element GS1, GS2, GS3 is assigned for example a new temperature for its operation by the neural network NN. In this way the detection of the desired gases or scents can be improved. A final weighting Gv or a result gas A, B, C is fed back to the input as additional neuron as feedback. This allows to detect gas mixtures easier.

FIGS. 3b to 3c show different random feedback loop structures of the neural network NN.

FIG. 3b: Feedback Alignment (FA)

FIG. 3c: Direct Feedback Alignment (DFA)

FIG. 3d: Indirect Feedback Alignment (IFA)

For the different algorithms the hidden layer update directions are determined as:

For FA, the hidden layer update directions are calculated as $$\delta a_2 = (B_2 e) \odot f'(a_2), \delta a_1 = (B_1 \delta a_2) \odot f'(a_1) \qquad \text{Eq. (7)}$$

where $B_1$ is a fixed random weight matrix with appropriate dimension. For DFA, the hidden layer update directions are calculated as $$\delta a_2 = (B_2 e) \odot f'(a_2), \delta a_1 = (B_1 e) \odot f'(a_1) \qquad \text{Eq. (8)}$$

where $B_1$ is a fixed random weight matrix with appropriate dimension. If all hidden layers have the same number of neurons, $B_1$ can be chosen identical for all hidden layers. For IFA, the hidden layer update directions are calculated as $$\delta a_2 = (W_2 \delta a_1) \odot f'(a_2), \delta a_1 = (B_1 e) \odot f'(a_1) \qquad \text{Eq. (9)}$$

where $B_1$ is a fixed random weight matrix with appropriate dimension. Ignoring the learning rate, the weight updates for all methods are calculated as $$\delta W_1 = -\delta a_1 x^T, \delta W_2 = -\delta a_2 h_1^T \delta W_3 = -e h_2^T \qquad \text{Eq. (10)}$$

While feedback alignment implementation looks almost similar to backpropagation, it uses a random matrix. It shows that neural networks NN can learn just fine using random matrices, without using the weight matrices.

With Direct Feedback Alignment, one can just use the gradient from the last layer to train all layers in neural networks NN. The individual layers do not necessarily depend on the gradient from their respective preceding layers. So, the training process does not have to progress layer by layer anymore.

Indirect Feedback Alignment is also an interesting option. Training a layer by means of a feedback from a layer in front of it is possible.

For the fixed-random matrix $B_i$ in particular temperature tensors or electrical field strength tensors are used.

Figure 5:
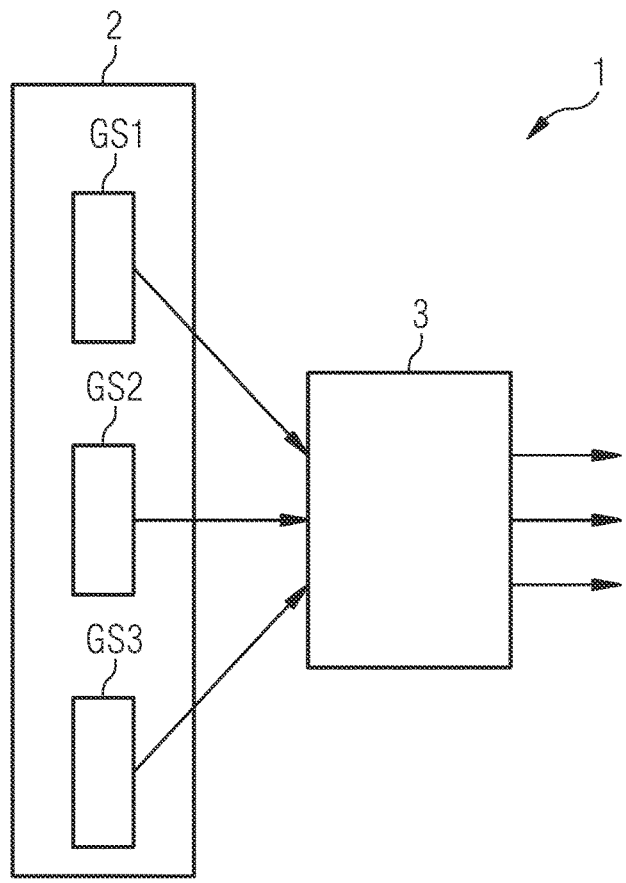
FIG. 5 an exemplary block diagram of an embodiment of a gas sensor system.

FIG. 5 shows a block diagram of a gas sensor system 1. The gas sensor system 1 comprises a gas sensor 2 and a hardware unit, for example an application-specific integrated circuit (ASIC).

The gas sensor 2 comprises at least one gas sensor element GS1, GS2, GS3. For example the gas sensor 2 is a multi-gas sensor as shown in FIG. 4.

The hardware unit (FIG. 5) is for example configured to power the gas sensor 2 and/or to measure the sensing signal s1, s2, s3 of the gas sensor elements GS1, GS2, GS3 of the gas sensor 2, in particular to measure the voltages of the gas sensor elements GS1, GS2, GS3. Furthermore, the ASIC is configured to randomly feedback the different temperature tensors to the neural network NN of the gas sensor system 1.

Figure 3:
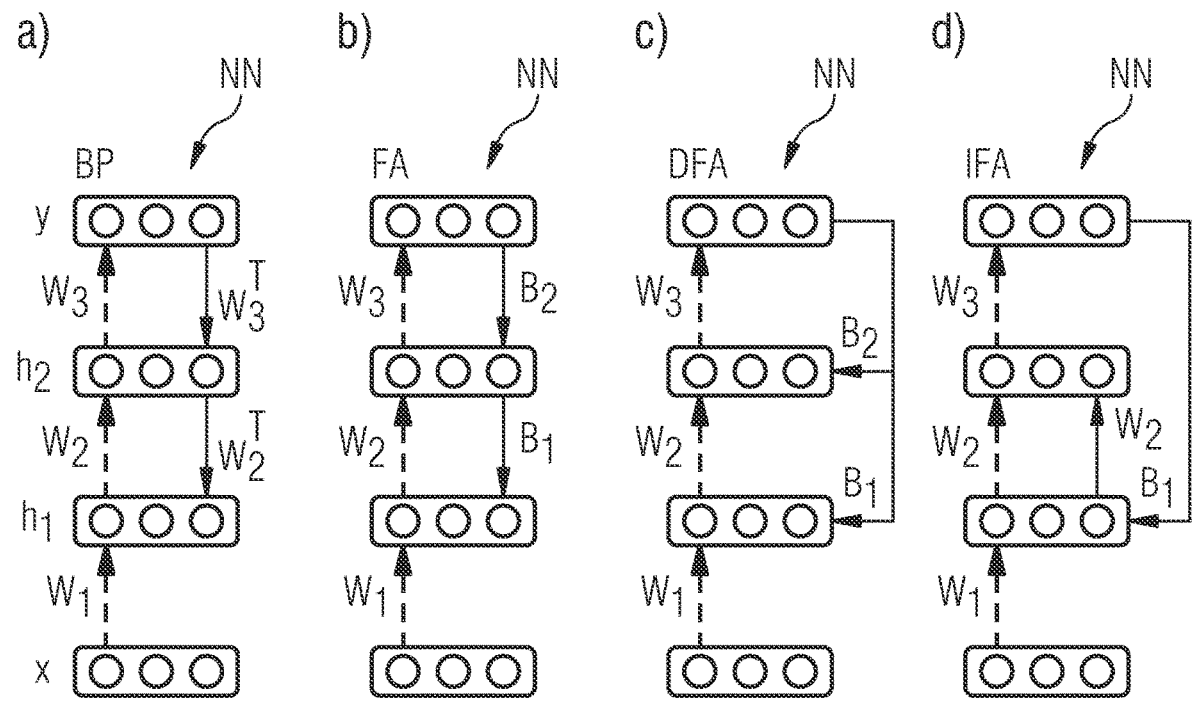
FIG. 3a an exemplary embodiment of an error feedback back propagation training method of the neural network.
FIG. 3b an exemplary embodiment of a Feedback Alignment training method.
FIG. 3c an exemplary embodiment of a Direct Feedback Alignment training method.
FIG. 3d an exemplary embodiment of an Indirect Feedback Alignment training method.

The hardware unit optionally comprises a memory unit that is configured to perform the processing of the trained neural network NN and to train the neural network NN based on at least one feedback alignment algorithm already mentioned with regard to FIG. 3.

Alternatively or additionally the gas sensor system 1 comprises an additional processing unit.

Figure 6:
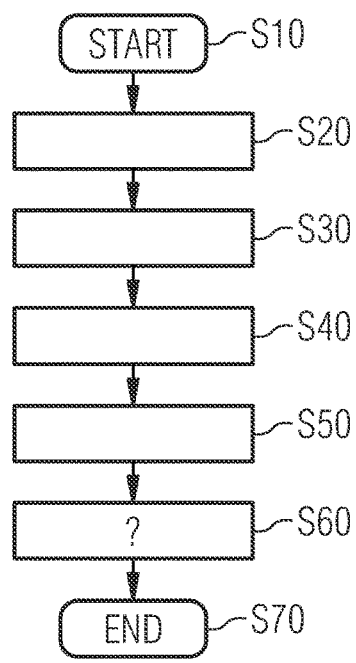
FIG. 6 a flow chart of an exemplary program to operate a gas sensor.

FIG. 6 shows a flow chart of an exemplary program to operate a gas sensor 2.

In a step S10 the program is started. During starting the program variables and/or objects may be initialized.

In a step S20 a first temperature matrix is selected and the heating of the senor element is controlled according to the temperature matrix. For instance, the first temperature matrix is stored on the Application Specific Integrated Circuit (ASIC).

In a step S30 measurement data of the gas sensor elements GS1, GS2, GS3 of the gas sensor 2 is captured. For example, the gas sensor elements GS1, GS2, GS3 provide resistance values or voltage values, which can be transformed to resistance values.

In a step S40 a weighting of the respective neuron is determined and based on the neural network NN the linkage of the respective neuron is determined.

In a Step S50 the respective gas is identified with a certain probability.

In a step S60 depending on the probability, temperature changes are applied (random temperature matrix etc.) improve the probability and/or to detect gas mixtures by means of the temperature changes (random temperature matrix etc.) and providing a feedback into the input layer of the neural network NN.

In a step S70 program ends.

The program described above uses for example a calibrated gas sensor, thus corresponding reference values are available. Alternatively or additionally reference values can be downloaded from the Cloud.

What is claimed is:

1. A method for operating a gas sensor, the method comprising:
   providing, by at least one gas sensor element, a sensing signal; and
   correcting, by a neural network, the sensing signal,
   wherein the neural network comprises an input layer, an output layer and at least one hidden layer,
   wherein the input layer comprises a given number k>1 of input neurons for each gas sensor element, and
   wherein a respective gas sensor element provides its sensing signal to one of the corresponding input neurons dependent on a measurement parameter applied to the at least one gas sensor element.

2. The method according to claim 1, wherein the gas sensor is operable in a learning mode using the neural network adjusted with random feedback loops between directly adjacent layers.

3. The method according to claim 2, wherein the random feedback loops comprise different temperature values.

4. The method according to claim 2, wherein the random feedback loops comprise different electrical field strength values.

5. The method according to claim 1, wherein the gas sensor is operable in a normal operation mode using the neural network with a feedforward structure.

6. The method according to claim 1, wherein the at least one gas sensor element comprises a semiconductor substrate with a metal oxide sensing layer.

7. The method according to claim 1, wherein the at least one gas sensor element comprises electrically conductive polymers.

8. The method according to claim 1, wherein the measurement parameter applied to the at least one gas sensor element is representative of a temperature of a sensing layer of the at least one gas sensor element.

9. The method according to claim 1, wherein the measurement parameter applied to the at least one gas sensor element is representative of an electrical field strength.

10. A gas sensor system comprising:
    at least one gas sensor element configured to provide a sensing signal; and
    an apparatus configured to receive the sensing signal and comprising a neural network configured to correct the sensing signal,
    wherein the neural network comprises an input layer, an output layer and at least one hidden layer,
    wherein the input layer comprises a given number k>1 of input neurons for each gas sensor element, and
    wherein a respective gas sensor element is configured to provide its sensing signal to one of the corresponding input neurons of the respective gas sensor element dependent on a measurement parameter applied to the respective gas sensor element.

11. The gas sensor system according to claim 10, further comprising an application-specific integrated circuit (ASIC) configured to provide random feedback weights to the neural network.

12. The gas sensor system according to claim 11, wherein the ASIC is configured to execute processing of a trained neural network in a normal operation mode of the gas sensor system.

13. The gas sensor system according to claim 11, wherein the ASIC is configured to:
- provide learning data; and
- provide random feedback weights for random feedback loops to the neural network for executing processing of the neural network in a learning mode.

\* \* \* \* \*